(12) United States Patent
Hamann et al.

(10) Patent No.: US 6,191,319 B1
(45) Date of Patent: Feb. 20, 2001

(54) PROCESS FOR PREPARING ALKALI METAL ALKOXIDES OF HIGHER ALCOHOLS

(75) Inventors: Carl Heinz Hamann, Ovelgönne; Jörg Helling, Bensheim; Peter Schmittinger, Unterhaching, all of (DE)

(73) Assignee: Degussa-Huels Aktiengesellschaft, Frankfurt (DE)

( * ) Notice: Under 35 U.S.C. 154(b), the term of this patent shall be extended for 0 days.

(21) Appl. No.: 09/458,016

(22) Filed: Dec. 10, 1999

(30) Foreign Application Priority Data

Jan. 5, 1999 (DE) ................................. 199 00 073

(51) Int. Cl.[7] .................................................. C07C 31/30
(52) U.S. Cl. .............................................................. 568/851
(58) Field of Search ............................................. 568/851

(56) References Cited

U.S. PATENT DOCUMENTS

| | | | |
|---|---|---|---|
| 4,596,895 | * | 6/1986 | Auschner et al. .................... 568/851 |
| 5,262,133 | * | 11/1993 | Adams et al. ........................ 423/180 |
| 5,942,647 | * | 8/1999 | Hamann et al. ..................... 568/851 |

* cited by examiner

Primary Examiner—Johann Richter
Assistant Examiner—Brian J. Davis
(74) Attorney, Agent, or Firm—Oblon, Spivak, McClelland, Maier & Neustadt, P.C.

(57) ABSTRACT

A process for preparing alkali metal alkoxides of alcohols comprising reacting an alkali metal amalgam with an alcohol having at least 3 carbon atoms in the presence of a powder catalyst comprising a transition metal carbide, nitride or carbonitride, to form a reaction mixture, wherein the reaction mixture is subjected to ultrasound during reaction.

20 Claims, No Drawings

PROCESS FOR PREPARING ALKALI METAL ALKOXIDES OF HIGHER ALCOHOLS

BACKGROUND OF THE INVENTION

1. Field of the Invention

The invention relates to a process for preparing alkali metal alkoxides of higher alcohols from an alkali metal amalgam and the free alcohol.

2. Discussion of the Background

Alkali metal alkoxides are important intermediates for, inter alia, the pharmaceutical industry. They are also used as catalysts in the synthesis of many organic compounds. The alkoxides of sodium and potassium have achieved particular industrial importance. A number of methods are known for preparing alkali metal alkoxides (F. A. Dickes, Ber. Dtsch. Chem. Ges. 63, 2753 [1930]). Solutions of alkali metal hydroxides in an alcohol contain the corresponding alkali metal alkoxide in equilibrium. Removal of the water present in this equilibrium, e.g. by distillation, gives pure alkoxides. However, a large amount of energy is required for this method of shifting the equilibrium, particularly in the case of low-boiling alcohols.

Alkali metal alkoxides are obtained directly by "dissolving" an alkali metal in the corresponding alcohol. Here, sodium and potassium react violently with lower alcohols such as methanol and ethanol with evolution of hydrogen. The less reactive higher alcohols such as propanols and butanols are preferably reacted at above the melting point of the respective alkali metal, possibly under superatmospheric pressure while stirring.

However, alkali metals are expensive starting materials for the preparation of alkoxides. It is more economical to use the inexpensive, liquid alkali metal amalgams obtained in chloralkali electrolysis by the mercury process as alkali metal source. The use of catalysts for accelerating the reaction of alkali metal amalgam and alcohol is also known. Thus, the process described in EP-A-O 177 768 uses a bed of granular anthracite whose surface is coated with a heavy metal oxide or a mixture of heavy metal oxides. Alkali metal amalgam and alcohol are fed in continuously in a counter-current manner and the alkali metal alkoxides are taken off continuously. A disadvantage of this process is that, in the preparation of alkali metal alkoxides of higher alcohols at acceptable reaction times, only from 60 to 80% of the alkali metal introduced in the form of the alkali metal amalgam can be reacted.

According to the proposal of German Patent Application 198 02 013.9, the alkali metal present in the alkali metal amalgam can be reacted to a greater extent even with higher alcohols at acceptable reaction times if the reaction is carried out in the presence of powder catalysts comprising transition metal carbides, nitrides or carbonitrides. Particularly suitable metals are molybdenum and tungsten and, of these, the carbides are particularly suitable. The powder catalysts are advantageously used at a mean particle diameter of from 1 to 10 $\mu$m. The reaction is therefore referred to as a micro-heterogeneously catalyzed reaction.

SUMMARY OF THE INVENTION

It has now surprisingly been found that the reaction rate and thus the spacetime yield in the preparation of alkali metal alkoxides of higher alcohols, i.e., alcohols having at least 3 carbon atoms, by reaction of an alkali metal amalgam with the free alcohol in the presence of a powder catalyst comprising a transition metal carbide, nitride or carbonitride is considerably increased if ultrasound is allowed to act on the reaction mixture during the reaction.

DETAILED DESCRIPTION OF THE INVENTION

The new process allows the preparation of alkali metal alkoxides at an up to 10 times higher reaction rate or space-time yield compared to a reaction carried out without ultrasound under otherwise identical conditions. This is surprising because slow reactions (with a reaction-controlled rate) cannot usually be accelerated appreciably by increasing the mixing (i.e. more rapid mass transfer to the catalyst surface). As a result of the higher reaction rate, a considerably greater quantity of alkali metal alkoxides can be prepared in existing equipment or new plants for a desired capacity can be made considerably smaller. This advantage is gained at a comparatively low additional equipment cost and energy consumption.

The process is particularly suitable for the reaction of alcohols having from 3 to 7 carbon atoms and a primary, secondary or tertiary carbinol group. Surprisingly, even the notoriously unreactive alcohols having a tertiary carbinol group can be reacted at a good reaction rate. Alcohols having more than seven carbon atoms can likewise be converted into their alkali metal alkoxides by the process of the invention, although the reaction rate decreases with increasing number of carbon atoms, even at elevated temperatures. The alcohols are preferably alkanols, but olefinic double bonds or one or two heteroatoms, for example ether oxygen atoms, may also be present in the carbon chain. Phenols and cresols are also considered to be higher alcohols for the purposes of the present invention. Examples of suitable higher alcohols are 1- and 2-propanol, 1- and 2-butanol, 2-methyl-1-propanol (isobutanol), 2-methyl-2-propanol (tert-butanol), 1-, 2- and 3-pentanol, 2-methyl-1-butanol, 2,2-dimethyl-1-propanol (neopentyl alcohol), 1-, 2- and 3-hexanol, 2-propen-1-ol (allyl alcohol), 2-buten-1-ol (butenol), 3-oxa-1-pentanol (ethyl glycol), phenol and o-, m- and p-cresol. The higher alcohol is advantageously used in an excess of up to 20 times, in particular from 5 to 15 times, the stoichiometric amount, based on the alkali metal, and, if desired, the excess higher alcohol is separated from the alkali metal alkoxide formed, e.g. by distillation.

Preferred alkali metal amalgams are liquid sodium and potassium amalgams having alkali metal contents of from 0.1 to 1 percent by weight, in particular from 0.3 to 0.6 percent by weight. Such alkali metal amalgams are available in industrial amounts from chloralkali electrolysis by the amalgam process.

The use of a transition metal carbide, nitride and/or carbonitride as described in German Patent Application 198 02 013.9 is an essential feature of the process of the present invention. Without the microheterogeneous catalyst, virtually no reaction of the alcohol with the alkali metal amalgam occurs even when using ultrasound. The preferred catalysts and particle sizes are as stated above. The mean particle diameter is preferably from 1 to 5 $\mu$m, in particular from 2 to 3 $\mu$m. The catalyst is preferably used in amounts of from 1 to 10 percent by weight, based on the higher alcohol.

The use of ultrasound for promoting the reaction is a further essential feature of the invention. A broad spectrum of frequencies is suitable for this purpose. Preference is given to using ultrasound at more than 16 kHz, in particular from 20 to 40 kHz. The specified frequencies include ranges which are still audible to the ears of young human beings.

For the purposes of the present invention, these ranges are also counted as ultrasound. There is also a wide freedom of choice in respect of the amplitude (or the specific energy input). The amplitude is advantageously at least 0.1 W/cm$^2$. Amplitudes of, for example, from 0.2 to 20 W/cm$^2$ have been found to be useful. Use is made of customary ultrasound generators such as ultrasonic probes for direct introduction of ultrasound or ultrasonic baths for indirect introduction.

The process of the invention can be carried out at room temperature (i.e. 20° C.) or at the temperature which is established as a result of the exothermic reaction. Particularly in the case of alcohols having 4 or more carbon atoms and a secondary or tertiary carbinol group, it can be desirable in the interests of an acceptable reaction rate to introduce additional heat indirectly. In general, the reaction is carried out at temperatures up to the boiling point of the respective alcohol and at atmospheric pressure.

The process of the invention is generally carried out without using an inert solvent or diluent. However, particularly in the case of alcohols having five or more carbon atoms which are relatively viscous at the reaction temperatures, the addition of a low-viscosity solvent or diluent can have a favorable effect on the reaction rate. Suitable inert solvents or diluents are, for example, ethers such as diethyl ether and tetrahydrofuran.

The process of the invention can, for example, be carried out batchwise by covering the alkali metal amalgam with the alcohol/catalyst phase, stirring to provide good contact between the phases and allowing ultrasound to act on the reaction mixture. Stirring or another form of mechanical mixing can be omitted if ultrasound having a high amplitude is employed. The reaction is complete as soon as evolution of hydrogen ceases. The reaction time is generally from 2 to 20 hours.

However, the process is advantageously carried out continuously using a method analogous to the decomposition of alkali metal amalgam with water for preparing alkali metal hydroxides, by conveying the alkali metal amalgam and alcohol/catalyst phases in a concurrent or countercurrent manner.

In both cases, the conversions are up to 100% based on the alkali metal in the alkali metal amalgam. After phase separation, the mercury can be returned to the chloralkali electrolysis and the alkali metal alkoxide can be isolated from the alcohol phase, advantageously by distilling off the excess alcohol, if appropriate after separating off the catalyst.

The following examples illustrate the invention but do not limit the scope of the invention as defined in the claims.

EXAMPLES

Example 1

In a 2 l round-bottom flask in an oil-filled, heated ultrasonic bath, 2,700 g of potassium amalgam having a potassium metal content of 15.6 g (0.40 mol) were stirred at 80° C. with 390 g (5.26 mol) of tert-butanol and 30 g (0.15 mol) of molybdenum carbide powder having an average particle diameter of 2 μm. The (indirect) sound input was about 0.25 W/cm$^2$ at 35 kHz.

After 2.5 hours, the reaction was stopped. The alcoholic phase was decanted from the amalgam and filtered to separate off powder catalyst. The residual alkali metal content of the amalgam (determined by gas-volumetric analysis in the decomposition of an amalgam sample with sulfuric acid) was 5.2 g (0.13 mol). In the alcoholic phase, 0.66 g (0.01 mol) of potassium hydroxide (determined by Karl Fischer titration) and 29.72 g (0.26 mol) of potassium tert-butoxide (KTB) (determined by acidimetric titration, taking into account the KOH content) were found. The conversion of the potassium metal after 2.5 hours was thus about 61%.

Example 2

The procedure of Example 1 was repeated using 2,700 g of potassium amalgam having an absolute potassium metal content of 14.85 g (0.38 mol) and 406 g (5.48 mol) of tert-butanol in the presence of 20 g (0.98 mol) of molybdenum carbide. After 18 hours, quantitative conversion of the potassium metal had been achieved and, in addition to KTB, 1.1 g of potassium hydroxide had been formed.

Example 3

In a 1 l round-bottom flask, 1,300 g of potassium amalgam comprising 9.49 g (0.234 mol) of potassium metal and 250 g of tert-butanol (3.37 mol) were reacted at 80° C. in the presence of 20 g (0.098 mol) of molybdenum carbide as described in Example 1. The energy input from an ultrasound generator having an ultrasonic probe which dipped into the reaction mixture was 15 W/cm$^2$ at 20 kHz. Mechanical stirring was omitted. After 5.5 hours, the conversion of the potassium metal present in the amalgam was 85%.

The disclosure of german priority patent application 199 00 073.5, filed Jan. 5, 1999, is hereby incorporated by reference.

What is claimed is:

1. A process for preparing alkali metal alkoxides of alcohols comprising reacting an alkali metal amalgam with an alcohol having at least 3 carbon atoms in the presence of a powder catalyst comprising a transition metal carbide, nitride or carbonitride, to form a reaction mixture, wherein the reaction mixture is subjected to ultrasound during reaction.

2. The process as claimed in claim 1, wherein the alcohol has from 3 to 7 carbon atoms and a primary, secondary or tertiary carbinol group.

3. The process as claimed in claim 1, wherein the alcohol is an alkanol or an alcohol having an olefinic double bond or one or two heteroatoms in the carbon chain.

4. The process as claimed in claim 1, wherein the alcohol is tert-butanol.

5. The process as claimed in claim 1, wherein the alcohol is used in an excess of up to 20 times the stoichiometric amount, based on the alkali metal in the alkali metal amalgam.

6. The process as claimed in claim 2, wherein the alcohol is used in an excess of up to 20 times the stoichiometric amount, based on the alkali metal in the alkali metal amalgam.

7. The process as claimed in claim 3, wherein the alcohol is used in an excess of up to 20 times the stoichiometric amount, based on the alkali metal in the alkali metal amalgam.

8. The process as claimed in claim 4, wherein the alcohol is used in an excess of up to 20 times the stoichiometric amount, based on the alkali metal in the alkali metal amalgam.

9. The process as claimed in claim 1, wherein the alkali metal amalgam is a sodium or potassium amalgam having an alkali metal content of from 0.1 to 1 percent by weight.

10. The process as claimed in claim 5, wherein the alkali metal amalgam is a sodium or potassium amalgam having an alkali metal content of from 0.1 to 1 percent by weight.

11. The process as claimed claim 1, wherein ultrasound of at least 16 kHz is employed.

12. The process as claimed claim 5, wherein ultrasound of at least 16 kHz is employed.

13. The process as claimed claim 9, wherein ultrasound of at least 16 kHz is employed.

14. The process as claimed claim 10, wherein ultrasound of at least 16 kHz is employed.

15. The process as claimed in claim 11, wherein ultrasound of a specific energy input of at least 0.1 W/cm$^2$ is employed.

16. The process as claimed in claim 12, wherein ultrasound of a specific energy input of at least 0.1 W/cm$^2$ is employed.

17. The process as claimed in claim 13, wherein ultrasound of a specific energy input of at least 0.1 is employed.

18. The process as claimed in claim 14, wherein ultrasound of a specific energy input of at least 0.1 W/cm$^2$ is employed.

19. The process as claimed in claim 1, wherein mercury from said amalgam is returned to a chloralkali electrolysis and the alkali metal alkoxide is isolated from an alcohol phase, optionally after separating off the catalyst.

20. The process as claimed in claim 5, wherein mercury from said amalgam is returned to a chloralkali electrolysis and the alkali metal alkoxide is isolated from an alcohol phase, optionally after separating off the catalyst.

* * * * *